United States Patent [19]

Cragle et al.

[11] Patent Number: 4,590,169

[45] Date of Patent: May 20, 1986

[54] DIRECT PARTICLE AGGLUTINATION IMMUNOASSAYS AVOIDING FALSE NEGATIVES AT HIGH ANTIGEN CONCENTRATIONS

[75] Inventors: Linda K. Cragle, San Diego; Paul C. Harris, Yorba Linda; Shih-Yun Lee, San Marcos; Ker-Kong Tung, Carlsbad; Morton A. Vodian, Escondido, all of Calif.

[73] Assignee: Beckman Instruments, Inc., Fullerton, Calif.

[21] Appl. No.: 553,209

[22] Filed: Nov. 18, 1983

[51] Int. Cl.$^4$ .............. G01N 33/543; G01N 33/546; G01N 33/555

[52] U.S. Cl. .................. 436/523; 436/519; 436/520; 436/533; 436/534; 436/829

[58] Field of Search ............ 436/523, 519, 520, 533, 436/534, 829

[56] References Cited

U.S. PATENT DOCUMENTS

| | | | |
|---|---|---|---|
| 4,115,535 | 9/1978 | Giaever | 436/523 X |
| 4,184,849 | 1/1980 | Cambiaso | 436/523 |
| 4,223,005 | 9/1980 | Teodorescu | 436/523 X |
| 4,279,617 | 7/1981 | Masson | 436/523 |
| 4,305,925 | 12/1981 | Kapmeyer | 436/523 X |
| 4,308,026 | 12/1981 | Mochida | 436/523 X |

*Primary Examiner*—Sidney Marantz

*Attorney, Agent, or Firm*—W. H. May; A. Grant; R. S. Frieman

[57] ABSTRACT

A direct particle agglutination immunoassay for assaying an antigenic substance (Ag) in a fluid. The immunoassay is the type which comprises:

(a) contacting the fluid with an antibody (Ab) coated particle (P) to agglutinate the Ab coated particles; and (b) detecting the presence of agglutination.

The immunoassay is characterized in that the fluid is contacted with at least one additional entity selected from a group consisting of at least one different type of antibody ($Ab_a$) coated particle ($P_1$) and at least one different type of antibody ($Ab_b$). The $P_1$ is selected from a group consisting of P, at least one different particle ($P_2$), and mixtures thereof (P and $P_2$). Each type of $Ab_a$-$P_1$ and $Ab_b$ has a lower average affinity constant (K) for Ag than the K of Ab-P and the additional entity is present in an amount sufficient to avoid a high antigen false negative effect.

Also, a reagent of the type comprising Ab-P. The reagent is characterized in that it further comprises at least one additional entity selected from a group consisting of at least one different type of $Ab_a$-$P_1$ and at least one different type of $Ab_b$. Ab-P, $Ab_a$-$P_1$, and $Ab_b$ are as defined above.

14 Claims, No Drawings

DIRECT PARTICLE AGGLUTINATION IMMUNOASSAYS AVOIDING FALSE NEGATIVES AT HIGH ANTIGEN CONCENTRATIONS

BACKGROUND OF THE INVENTION

1. Field of the Invention

This invention relates to a direct particle agglutination immunoassay and to a kit for use therein.

2. Description of the Prior Art

Most particle agglutination immunoassays are performed using an indirect methodology. In this methodology a particle (usually polystyrene latex) is covered with an antigen. A test sample (containing free antigen) is mixed with a predetermined amount of antibody and after a short incubation time, the particulate suspension is added. If antigen is present in the test sample the antibody is consumed and is not available to bind to and crosslink (agglutinate) the antigen coated particles in the subsequent reaction. If no antigen is present in the patient sample the antibody acts to agglutinate the particulate material by bridging the antigens on adjacent particle surfaces.

The indirect particle agglutination methodology is used primarily because false negative results are not obtained for patient samples having high antigen concentrations. For various reasons, the indirect agglutination procedure is not the preferred method. One reason is that this methodology can be quite costly because each test requires both an antibody and a purified antigen. Another reason is that this methodology is tedious and time consuming in that it requires two steps, namely, the pre-incubation of the sample with the antibody and the subsequent addition of the particulate suspension.

The preferred agglutination methodology is the direct particle agglutination assay. In this method the particulate material is covered with the antibody. These antibody particles are mixed with the patient sample directly. If antigen exists in the sample, the antibody binds the antigen and the particles become aggregated. If no antigen is present, no reactio occurs. Accordingly, the direct agglutination assay requires a multi-determinant antigen and heterogenous antibody which can either be a polyclonal antibody or a mixture of monoclonal antibodies wherein each type of monoclonal antibody is specific for a different determinant site. However, the direct agglutination assay does not require purified antigen for each assay and requires only one step to perform the test. Unfortunately, the direct agglutination assay is not often used because at high antigen concentrations (as can be found with certain analytes like HCG) the particles become completely coated with antigen and the desired agglutination is thereby inhibited, thus yielding a false negative result.

Accordingly, it would be very desirable to have a direct particle agglutination assay and kit wherein the false negative result is either prevented or avoided.

SUMMARY OF THE INVENTION

In accordance with the present invention, there are provided an improved direct particle agglutination assay and kit for use therein wherein all the advantages possessed by the prior direct particle agglutination assays are maintained with the concurrent avoidance of the false negative result at high antigen concentrations.

More particularly, the present invention encompasses an improved direct particle agglutination assay for assaying an antigenic substance (Ag) in a fluid. The assay of the present invention is of the type which comprises:

(a) contacting the fluid with an antibody (Ab) coated particle (P) to agglutinate the Ab antibody coated particles (Ab-P); and (b) detecting the presence of agglutination.

The improved direct particle agglutination assay of this invention is characterized in that the fluid is contacted with at least one additional entity selected from a group consisting of one or more different type of antibody ($Ab_a$) coated particle ($P_1$), one or more different type of antibodies ($Ab_b$), and mixtures thereof;

wherein:

(i) $P_1$ is selected from a group consisting of P, one or more different particles ($P_2$), and mixtures thereof (P and $P_2$);

(ii) each different type of $Ab_a$-$P_1$ and $Ab_b$ has a lower average affinity constant (K) for Ag than the K of Ab-P for Ag; and (iii) the additional entity is present in an amount sufficient to avoid the false negative result at high antigen concentrations.

Also within the scope of this invention is an improved reagent. The improved reagent is of the type comprising Ab-P. The reagent of the present invention is characterized in that it further comprises at least one additional entity selected from a group consisting of one or more different types of $Ab_a$ coated $P_1$, one or more different types of $Ab_b$, and mixtures thereof;

wherein:

(i) Ab-P, $Ab_A$-$P_1$, and $Ab_b$ are as described above; and (ii) the additional entity is present in an amount sufficient to avoid the false negative result at high antigen concentrations when the reagent is employed in the direct particle agglutination assay.

DESCRIPTION OF THE PREFERRED EMBODIMENTS

The average affinity constant (K) for each different type of $Ab_a$-$P_1$ and $Ab_b$ for Ag must the lower than the K of Ab-P for Ag. This restriction assures that the former entities compete at most only insignificantly with the latter entity in the dynamic range. In order to achieve this result, it is preferred that each K of each different type of $Ab_a$-$P_1$ and $Ab_b$ for Ag be at least 5, more preferably at least 10, times lower than the K of Ab-P for Ag.

In addition, the higher the antigen concentrations at which one wishes to extend the avoidance of the false negative result, the larger the difference must be between the respective K of Ab-P and the K of $Ab_a$-$P_1$ and $Ab_b$.

When more than one type of $Ab_a$-$P_1$ or $Ab_b$ is employed, each such type preferably has a different K.

The amount of $Ab_a$-$P_1$ employed can be any amount sufficient to avoid the high antigen false negative effect. More particularly, this amount can range from about 10% to about 200% of the concentration of Ab-P.

The amount of $Ab_b$ employed can be any amount sufficient to avoid the high antigen false negative effect. More particularly, this amount can range from 10% to about 200% of the concentration of Ab-P.

In order to obtain the advantages of the present invention, one need only additionally employ either $Ab_a$-$P_1$ or $Ab_b$. It is preferred to only employ $Ab_b$ as the additional entity. It is also preferred to employ $Ab_a$-$P_1$ wherein $P_1$ is selected from the group consisting of one or more different particles ($P_2$).

Ab, $Ab_a$ and $Ab_b$ are each independently selected from a group consisting of monoclonal antibodies, polyclonal antibodies, and mixtures thereof.

Any small particle that one can bind an antibody to and obtain an agglutinatable composition can be employed in the instant invention. Such particles include, but are not limited to, liposomes, fixed red blood cells, bacteria, and polystyrene latex. Preferably, the particle is polystyrene latex.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A direct particle agglutination assay for an antigenic substance (Ag) in a fluid comprising:
   (a) contacting said fluid with an antibody (Ab) coated particle (P) to agglutinate the Ab coated particles; and
   (b) detecting the presence of agglutination; the improvement wherein said fluid is contacted with an additional entity comprising at least one different type of antibody ($Ab_a$) coated particle ($P_1$); wherein:
      (i) $P_1$ is selected from the group consisting of P, at least one different particle ($P_2$), and mixtures thereof (P and $P_2$);
      (ii) each type of $Ab_a$-$P_1$ has a lower average affinity constant (K) for Ag than the K of Ab-P; and
      (iii) said additional entity is present in an amount sufficient to avoid a high antigen false negative effect.

2. The assay of claim 1 wherein each K of each different type of $Ab_a$-$P_1$ for Ag is at least 5 times lower than said K of Ab-P for Ag.

3. The assay of claim 1 wherein each K of each different type of $Ab_a$-$P_1$ for Ag is at least 10 times lower than said K of Ab-P for Ag.

4. The assay of claim 1 wherein said additional entity is said $Ab_a$-$P_1$, wherein said $P_1$ is selected from said group consisting of at least one different solid carrier ($P_2$).

5. The assay of claim 4 wherein each K of each different type of $Ab_a$-$P_1$ for Ag is at least 5 times lower than said K of Ab-P for Ag.

6. The assay of claim 4 wherein each K of each different type of $Ab_a$-$P_1$ for Ag is at least 10 times lower than said K of Ab-P for Ag.

7. A reagent comprising an antibody (Ab) coated particle (P);
   the improvement wherein said reagent further comprises an additional entity comprising at least one different type of antibody ($Ab_a$) coated particle ($P_1$);
   wherein:
      (i) $P_1$ is selected from the group consisting of P, at least one different particle ($P_2$), and mixtures thereof (P and $P_2$);
      (ii) each type of $Ab_a$-$P_1$ has a lower average affinity constant (K) for Ag than the K of Ab-P; and
      (iii) said additional entity is present in an amount sufficient to avoid a high antigen false negative effect when said reagent is employed in a direct particle agglutination assay.

8. The reagent of claim 7 wherein each K of each different type of $Ab_a$-$P_1$ for Ag is at least 5 times lower than said K of Ab-P for Ag.

9. The reagent of claim 7 wherein each K of each different type of $Ab_a$-$P_1$ for Ag is at least 10 times lower than said K of Ab-P for Ag.

10. The reagent of claim 7 wherein said additional entity is present in a concentration of about 10% to about 200% of the concentration of Ab-P.

11. The reagent of claim 7 wherein said additional entity is present in a concentration of about 10% to about 200% of the concentration of Ab-P.

12. The reagent of claim 7 wherein said additional entity is said $Ab_a$-$P_1$, wherein said $P_1$ is selected from said group consisting of at least one different particle ($P_2$).

13. The reagent of claim 12 wherein each K of each different type of $Ab_a$-$P_1$ for Ag is at least 5 times lower than said K of Ab-P for Ag.

14. The reagent of claim 12 wherein each K of each different type of $Ab_a$-$P_1$ for Ag is at least 10 times lower than said K of Ab-P for Ag.

* * * * *